(12) United States Patent
Sorg et al.

(10) Patent No.: US 11,951,144 B2
(45) Date of Patent: Apr. 9, 2024

(54) COMPOSITION, FOOD SUPPLEMENT, COMPOSITION ACTING AS A FOOD SUPPLEMENT FOR CHILDREN, AND PRODUCTION METHOD

(71) Applicant: PM-INTERNATIONAL AG, Schengen (LU)

(72) Inventors: Rolf Sorg, Schengen (LU); Tobias Kühne, Morbach (DE); Christian Lauinger, Ettlingen (DE); Wilhelm Messer, Bad Dürkheim (DE)

(73) Assignee: PM—INTERNATIONAL AG, Schengen (LU)

( * ) Notice: Subject to any disclaimer, the term of this patent is extended or adjusted under 35 U.S.C. 154(b) by 278 days.

(21) Appl. No.: 17/268,316

(22) PCT Filed: Sep. 12, 2018

(86) PCT No.: PCT/EP2018/074588
§ 371 (c)(1),
(2) Date: Feb. 12, 2021

(87) PCT Pub. No.: WO2020/052745
PCT Pub. Date: Mar. 19, 2020

(65) Prior Publication Data
US 2022/0110994 A1    Apr. 14, 2022

(51) Int. Cl.
| | | |
|---|---|---|
| A61K 36/00 | (2006.01) |
| A23L 33/105 | (2016.01) |
| A23L 33/125 | (2016.01) |
| A23L 33/135 | (2016.01) |
| A23L 33/14 | (2016.01) |
| A23L 33/15 | (2016.01) |
| A23L 33/16 | (2016.01) |
| A23L 33/22 | (2016.01) |
| A61K 31/12 | (2006.01) |
| A61K 31/197 | (2006.01) |
| A61K 31/355 | (2006.01) |
| A61K 31/375 | (2006.01) |
| A61K 31/4188 | (2006.01) |
| A61K 31/4415 | (2006.01) |
| A61K 31/455 | (2006.01) |
| A61K 31/51 | (2006.01) |
| A61K 31/519 | (2006.01) |
| A61K 31/522 | (2006.01) |
| A61K 31/525 | (2006.01) |
| A61K 31/593 | (2006.01) |
| A61K 31/714 | (2006.01) |
| A61K 33/06 | (2006.01) |
| A61K 33/30 | (2006.01) |
| A61K 33/34 | (2006.01) |
| A61K 35/20 | (2006.01) |
| A61K 36/064 | (2006.01) |
| A61K 36/67 | (2006.01) |
| A61K 36/9068 | (2006.01) |
| A61K 47/12 | (2006.01) |
| A61K 47/26 | (2006.01) |
| A61K 47/36 | (2006.01) |
| A61K 47/46 | (2006.01) |
| A61K 47/69 | (2017.01) |

(52) U.S. Cl.
CPC ............ *A61K 36/67* (2013.01); *A23L 33/105* (2016.08); *A23L 33/125* (2016.08); *A23L 33/135* (2016.08); *A23L 33/14* (2016.08); *A23L 33/15* (2016.08); *A23L 33/16* (2016.08); *A23L 33/22* (2016.08); *A61K 31/12* (2013.01); *A61K 31/197* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/522* (2013.01); *A61K 31/525* (2013.01); *A61K 31/593* (2013.01); *A61K 31/714* (2013.01); *A61K 33/06* (2013.01); *A61K 33/30* (2013.01); *A61K 33/34* (2013.01); *A61K 35/20* (2013.01); *A61K 36/064* (2013.01); *A61K 36/9068* (2013.01); *A61K 47/12* (2013.01); *A61K 47/26* (2013.01); *A61K 47/36* (2013.01); *A61K 47/46* (2013.01); *A61K 47/6951* (2017.08); *A23V 2002/00* (2013.01); *A23V 2400/113* (2023.08); *A23V 2400/173* (2023.08)

(58) Field of Classification Search
CPC ...................................................... A61K 36/00
See application file for complete search history.

(56) References Cited

U.S. PATENT DOCUMENTS

2011/0206721 A1    8/2011   Nair

FOREIGN PATENT DOCUMENTS

| EP | 2415358 A2 | 2/2012 |
| EP | 3345623 A1 | 7/2018 |

OTHER PUBLICATIONS

National Intellectual Property Administration, PRC, First Examination Report and Search Report, Application No. 201880097270.5, dated Nov. 30, 2022, 13 pages.

Munjal et al., Comparative Oral Bioavailability Advantage from Curcumin Formulations, Drug Delivery and Translational Research, 2011, 1:322-331.

Prasad et al., Recent Developments in Delivery, Bioavailability, Absorption and Metabolism of Curcumin: The Golden Pigment from Golden Spice, Cancer Research and Treatment, 2014, 46(1):2-18.

(Continued)

*Primary Examiner* — Rosanne Kosson
(74) *Attorney, Agent, or Firm* — Quarles & Brady LLP

(57) ABSTRACT

A composition, containing
a pepper component,
a curcumin-cyclodextrin mixture and
a mixture of fruits, vegetables and spices.

15 Claims, No Drawings

(56) References Cited

OTHER PUBLICATIONS

Mintel, KidGreenz Natural Tropical Fruit Flavour Children's Chewable Tablets, Product Information, Aug. 15, 2018, www.gnpd.com, 4 pages.

Mintel, Multi-Vitamin Dietary Supplement, Product Information, Dec. 22, 2017, www.gnpd.com, 5 pages.

PCT International Search Report and Written Opinion, PCT/EP2018/074588, dated Apr. 25, 2019, 28 pages.

COMPOSITION, FOOD SUPPLEMENT, COMPOSITION ACTING AS A FOOD SUPPLEMENT FOR CHILDREN, AND PRODUCTION METHOD

CROSS-REFERENCE TO RELATED APPLICATIONS

This application represents the national stage entry of PCT International Application No. PCT/EP2018/074588 filed on Sep. 12, 2018. The contents of this application is hereby incorporated by reference as if set forth in its entirety herein.

DESCRIPTION

The disclosure relates to a composition, a dietary supplement, a composition as a dietary supplement for children and a method for preparing a composition, a dietary supplement or a composition as a dietary supplement for children.

The use of dietary supplements, for example in sports or to promote health, is already known. Dietary supplements are also suitable for supplementing an unbalanced diet. In contrast to conventional foods and beverages, dietary supplements usually represent a concentrate of food additives or other substances with a nutrition-specific, physiological effect. They are marketed in dosed form, particularly in the form of capsules, pastilles, tablets, effervescent tablets, powder sachets, liquid ampoules and bottles with dropper inserts, for ingestion in measured small quantities. Often, a dietary supplement contains more than one specific substance, for example, several vitamins and/or minerals in a predetermined ratio. Some dietary supplements also contain certain antioxidants. Since synthetic compounds are used in the manufacture of most dietary supplements, the preparations often contain a manageable number of ingredients as a result. There is little to be said against the use of synthetic ingredients. However, this does not take advantage of the full power of nature. In particular, the large number of different plant secondary metabolites and polyphenols is not used to the extent that nature provides. Yet plant secondary metabolites such as polyphenols have been shown to have numerous health-promoting properties with synergistic effects.

Ultimately, dietary supplements provide the substances that the consumer needs in a corresponding situation, for example the athlete when practicing an endurance sport. Ultimately, however, it is not only decisive which substances are provided, but also how they are provided and the extent to which it is possible to make the dietary supplements available to the body and ultimately to the individual cell of the human body. This bioavailability is considered to be in need of improvement, especially when concentrated dietary supplements are administered.

It is therefore an object of the present disclosure to provide a composition, a dietary supplement and a composition as a dietary supplement for children, in which one or more components together with a mixture of a wide variety of plant secondary metabolites can develop their health-promoting effect in a synergistic manner and at the same time the bioavailability of the components is improved. Furthermore, a method is to be provided which enables such compositions and dietary supplements, in particular in homogeneous mixing.

According to the disclosure, this object is solved by a composition according to claim 1 and a dietary supplement according to claim 10. With regard to the composition as a dietary supplement for children, this object is solved by claim 11. With regard to the method for preparing a composition, a dietary supplement or a composition as a dietary supplement for children, this object is solved by claim 15.

Preferably, the disclosure is based on the idea of providing a composition, preferably containing a pepper component, a curcumin-cyclodextrin mixture and a mixture of fruits, vegetables and spices.

The mixture of fruits, vegetables and spices according to the disclosure preferably contains concentrates and extracts of a wide variety of plants and provides a variety of health-promoting plant secondary metabolites, vitamins and polyphenols.

A composition according to the disclosure can increase the bioavailability of the compounds contained in the composition. Therefore, a composition is obtained which has a particularly health-promoting effect and supports a balanced diet particularly well.

Another advantage is that the composition can be added to different dietary supplements with little effort, allowing different dietary supplements to benefit from the properties of the composition.

Preferred embodiments of the disclosure are given in the subclaims.

Preferably, the composition further comprises an algae component.

In preferred embodiments, the algae component is derived from brown algae.

In certain embodiments, algae and/or algae parts, in particular dried algae and/or algae parts, constitute the algae component.

In certain embodiments, the algae component is an algae powder or a powder of algae, in particular of dried algae. In particular, a powder of algae is obtained by grinding algae, in particular by grinding dried algae.

In certain embodiments, the algae component is an algae extract. In particular, an algae extract is obtained by means of organic and/or aqueous solvents, optionally under the action of heat. Optionally, the extract is dried after extraction.

In certain embodiments, the algae component is derived from brown algae, and in particular, the algae component is a powder of brown algae.

Algae contain valuable and natural organic substances and minerals.

Preferably, the composition further comprises an extract of ginger (*Zingiber officinale*). Preferably, it is an extract from the rhizome of ginger (*Zingiber officinale*). A ginger extract contains valuable and natural organic substances. In addition, a ginger extract is a bioenhancer, which increases the bioavailability of components of the composition.

Preferably, the pepper component is an extract from the pepper (*Piper nigrum*), in particular piperine.

A pepper extract or piperine increases the bioavailability of the components of the composition.

Preferably, the curcumin-cyclodextrin mixture is a curcumin-cyclodextrin complex. Most preferably, the curcumin-cyclodextrin mixture is a curcumin-gamma-cyclodextrin complex.

With such a formulation, curcumin can be absorbed and act particularly effectively.

In preferred embodiments, the mixture of fruits, vegetables, and spices includes an extract of green tea (*Camellia sinensis*), in particular green tea leaves, and a concentrate of broccoli (*Brassica oleracea italica*), in particular of seeds, sprouts and/or shoots of broccoli, and a concentrate of broccoli (*Brassica oleracea italica*), in particular florets and/or stems of broccoli, and an extract of the onion (*Allium cepa*, in particular *Allium cepa alliaceae*), in particular the bulb of the onion, and an extract of apple (*Malus domestica*), in particular of apple fruit, in particular of apple fruit peel, and an extract of acerola (*Malpighia glabra*, in particular *Malpighia glabra linne*), in particular the fruit of acerola, and a concentrate from tomato (*Lycopersicon esculentum*), in particular from the fruit of the tomato, and a concentrate from turmeric (*Curcuma longa*), in particular from the root of turmeric, and a concentrate from garlic (*Allium sativum*), especially from the garlic clove, and a concentrate of basil (*Ocimum basilicum*), in particular of basil leaves, and a concentrate of oregano (*Origanum vulgare*), especially leaves of oregano, and a concentrate from the cinnamon tree (*Cinnamonum cassia*), in particular from the bark (without cork) of the cinnamon tree, and a concentrate of carrot (*Dacus carota*, in particular *Dacus carota sativa*), especially the root of the carrot, and a concentrate from elderberry (*Sambucus nigra*), in particular from the fruit of the elderberry, and an extract of currant (*Ribes*), in particular of blackcurrant (*Ribes nigrum*), in particular of the fruit of the blackcurrant, and a concentrate from blueberry (*Vaccinium*), in particular from the fruit of the blueberry, and a concentrate from raspberry (*Rubus idaeus*), in particular from the fruit of the raspberry, and a concentrate of blackberry (*Rubus* spp.), especially the fruit of the blackberry, and a concentrate of chokeberry (*Aronia*, in particular *Aronia melanocarpa*), especially the fruit of the chokeberry, and a concentrate from spinach (*Spinacia oleracea*), in particular from the leaves of the spinach, and a concentrate from the cherry (*Prunus avium*), in particular from the cherry fruit, and a concentrate from Brussels sprouts (*Brassica oleracea gemmifera*), especially florets of Brussels sprouts.

It cannot be entirely ruled out that concentrates or extracts from other, especially related, plants and other parts of plants may be used in place of individual concentrates or extracts in this list to achieve a similar technical effect.

In certain embodiments, the mixture of fruits, vegetables, and spices contains an extract of green tea (*Camellia sinensis*), in particular of green tea leaves, and/or a concentrate of broccoli (*Brassica oleracea italica*), in particular of seeds, sprouts and/or shoots of broccoli, and/or a concentrate from broccoli (*Brassica oleracea italica*), in particular from florets and/or stems of broccoli, and/or an extract from the onion (*Allium cepa*, in particular *Allium cepa alliaceae*), in particular from the bulb of the onion, and/or an extract from apple (*Malus domestica*), in particular from the apple fruit, in particular from peels of the apple fruit, and/or an extract from acerola (*Malpighia glabra*, in particular *Malpighia glabra linne*), in particular from the fruit of acerola, and/or a concentrate from the tomato (*Lycopersicon esculentum*), in particular from the fruit of the tomato, and/or a concentrate from turmeric (*Curcuma longa*), in particular from the root of turmeric, and/or a concentrate from garlic (*Allium sativum*), in particular from the garlic clove, and/or a concentrate of basil (*Ocimum basilicum*), in particular of basil leaves, and/or a concentrate of oregano (*Origanum vulgare*), in particular of leaves of oregano, and/or a concentrate from the cinnamon tree (*Cinnamonum cassia*), in particular from the bark (without cork) of the cinnamon tree, and/or a concentrate from the carrot (*Dacus carota*, in particular *Dacus carota sativa*), in particular from the root of the carrot, and/or a concentrate from elderberry (*Sambucus nigra*), in particular from the fruit of the elderberry, and/or an extract of the currant (*Ribes*), in particular of the blackcurrant (*Ribes nigrum*), in particular of the fruit of the blackcurrant, and/or a concentrate from the blueberry (*Vaccinium*), in particular from the fruit of the blueberry, and/or a concentrate of raspberry (*Rubus idaeus*), in particular of the fruit of the raspberry, and/or a concentrate from the blackberry (*Rubus* spp.), in particular from the fruit of the blackberry, and/or a concentrate from the chokeberry (*Aronia*, in particular *Aronia melanocarpa*), especially from the fruit of the chokeberry, and/or a concentrate from spinach (*Spinacia oleracea*), in particular from the leaves of the spinach, and/or a concentrate from the cherry (*Prunus avium*), in particular from the cherry fruit, and/or a concentrate from Brussels sprouts (*Brassica oleracea gemmifera*), especially florets of Brussels sprouts.

The term "extract" (preferably with the exception of algae extract) means in the context of this patent application a dehydrated extract from corresponding plant parts, wherein the extract is preferably obtained with the aid of ethanol and water and with a drug-extract ratio between 90:1 and 15:1. A "concentrate" in the context of this patent application means a dehydrated product from corresponding plant parts. Extracts and concentrates from fruits, leaves, bulbs, bark (excluding cork), roots, rhizomes, tubers, seeds, sprouts, shoots, florets, and stems provide high levels of valuable plant-derived secondary metabolites such as polyphenols, depending on the plant species. Basically, one idea is to provide several extracts and concentrates from different plant species and parts in order to provide the highest possible content and, above all, the highest possible diversity of plant secondary metabolites and polyphenols. Therefore, a large number of extracts and concentrates from different plant parts of different plant species is preferred. Polyphenols are aromatic compounds that contain two or more hydroxyl groups directly attached to an aromatic ring and are classified as plant secondary metabolites. Polyphenols exhibit various health-promoting effects; in particular, some polyphenols have an antioxidant effect.

In preferred embodiments, 100 g of the composition contains 10 mg to 5000 mg, preferably 50 mg to 4000 mg, of the pepper component, 20 mg to 1000 mg, preferably 80 mg to 400 mg, of the curcumin-cyclodextrin mixture, and 50 mg to 1000 mg, preferably 100 mg to 500 mg, of the mixture of fruits, vegetables and spices. In addition, 100 g of the composition may optionally contain 1 mg to 1000 mg, preferably 5 mg to 60 mg, of the ginger (*Zingiber officinale*) extract and/or 5 mg to 500 mg, preferably 10 mg to 100 mg, of the algae component.

In preferred embodiments, the composition further comprises one or more components selected from:
- Vitamin C, preferably 500 mg to 2000 mg per 100 g of composition;
- Niacin, preferably 100 mg to 800 mg per 100 g of composition;
- Caffeine, preferably 50 mg to 500 mg per 100 g of composition;
- Alpha-tocopheryl acetate, preferably 20 mg to 300 mg per 100 g of composition;
- Pantothenic acid, preferably 20 mg to 100 mg per 100 g of composition;
- Pyridoxine, preferably 5 mg to 60 mg per 100 g of composition;
- Thiamine, preferably 5 mg to 60 mg per 100 g of composition;
- Riboflavin, preferably 4 mg to 40 mg per 100 g of composition;
- Cyanocobolamine, preferably 4 µg to 20 µg per 100 g of composition;
- Folic acid, preferably 0.5 mg to 5 mg per 100 g of composition;
- Biotin, preferably 0.5 mg to 5 mg per 100 g of composition;
- Beta-carotene, preferably 4 mg to 30 mg per 100 g of composition;
- Selenium-enriched yeast, preferably 10 mg to 500 mg per 100 g of composition.
- Gum arabic, preferably 10 g to 30 g per 100 g of composition;
- Vegetable fiber, preferably from oats, pea, rice and apple, preferably 10 g to 25 g per 100 g of composition;
- Pectin and/or guar gum, preferably totaling 1 g to 6 g;
- Guarana extract, preferably 1 g to 3 g per 100 g of composition;
- Lactic acid cultures (*Lactobacillus acidophilus, Lactobacillus reuteri*) preferably 0.1 g to 1 g per 100 g of composition;
- Inulin, preferably 0.1 g to 1 g per 100 g of composition;
- Grape seed extract, preferably 1 mg to 20 mg per 100 g of composition.

In preferred embodiments, the composition further comprises one or more components selected from:
- Citric acid, preferably 1 g to 5 g per 100 g of composition;
- Fructose, preferably 20 g to 70 g per 100 g of composition;
- Beetroot powder (concentrate of beetroot juice, maltodextrin and citric acid), preferably 0.1 g to 2 g per 100 g of composition;
- Multienzyme complex of amylase, lactase, protease, cellulase, lipase, preferably 0.1 g to 1 g per 100 g of composition;
- Steviol glycosides, preferably 0.01 g to 0.5 g per 100 g of composition.

In preferred embodiments, the composition is present as a powder. In preferred embodiments, the composition is present as a powder in capsules, sachets or cans, particularly in sachets. Most preferably, the composition is present as a powder in individual doses in sachets.

In certain embodiments, the composition is suitable for preparing an aqueous solution in water. In certain embodiments, the composition is suitable for preparing a suspension in water.

The disclosure is further based on the idea of providing a dietary supplement containing a composition according to the disclosure.

For advantages and embodiments of the dietary supplement, reference is made to the advantages and embodiments of the composition.

In preferred embodiments, the dietary supplement is present as a powder. In preferred embodiments, the dietary supplement is present as a powder in capsules, sachets or cans, in particular in sachets. Very preferably, the dietary supplement is present as a powder in individual doses in sachets.

In certain embodiments, the dietary supplement is suitable for preparing an aqueous solution in water. In certain embodiments, the dietary supplement is suitable for preparing a suspension in water.

The disclosure is further based on the idea of providing a composition as a dietary supplement for children.

Preferably, the disclosure is based on the idea of providing a composition as a dietary supplement for children, wherein the composition preferably comprises a pepper component, a curcumin-cyclodextrin mixture, and a mixture of fruits, vegetables, and spices.

In other words, a composition is to be provided which has similar effects and advantages as the composition described above, but which is specifically designed in its composition to meet the needs and sensitivities of children. Previous explanations and descriptions of the composition according to the disclosure and its advantages therefore also apply to the composition as a dietary supplement for children, unless the following indicates otherwise.

Preferably, the pepper component is an extract from the pepper (*Piper nigrum*), in particular piperine.

A pepper extract or piperine increases the bioavailability of the components of a dietary supplement.

Preferably, the curcumin-cyclodextrin mixture is a curcumin-cyclodextrin complex. Particularly preferably, the curcumin-cyclodextrin mixture is a curcumin-gamma-cyclodextrin complex. Such curcumin-gamma-cyclodextrin complexes are commercially available.

With such a formulation, curcumin can be absorbed and act particularly effectively.

In preferred embodiments, the mixture of fruits, vegetables, and spices includes an extract of green tea (*Camellia sinensis*), in particular green tea leaves, and
- a concentrate of broccoli (*Brassica oleracea italica*), in particular of seeds, sprouts and/or shoots of broccoli, and
- a concentrate of broccoli (*Brassica oleracea italica*), in particular florets and/or stems of broccoli, and
- an extract of the onion (*Allium cepa*, in particular *Allium cepa alliaceae*), in particular the bulb of the onion, and
- an extract of apple (*Malus domestica*), in particular of apple fruit, in particular of apple fruit peel, and
- an extract of acerola (*Malpighia glabra*, in particular *Malpighia glabra linne*), in particular the fruit of acerola, and
- a concentrate from tomato (*Lycopersicon esculentum*), in particular from the fruit of the tomato, and
- a concentrate from turmeric (*Curcuma longa*), in particular from the root of turmeric, and
- a concentrate from garlic (*Allium sativum*), especially from the garlic clove, and a concentrate of basil (*Ocimum basilicum*), in particular of basil leaves, and a concentrate of oregano (*Origanum vulgare*), especially leaves of oregano, and a concentrate from the cinnamon tree (*Cinnamomum cassia*), in particular from the bark (without cork) of the cinnamon tree, and a concentrate of carrot (*Dacus carota*, in particular *Dacus carota sativa*), especially the root of the carrot, and a concentrate from elderberry (*Sambucus nigra*), in particular from the fruit of the elderberry, and an extract of currant (*Ribes*), in particular of blackcurrant (*Ribes nigrum*), in particular of the fruit of the blackcurrant, and a concentrate from blueberry (*Vaccinium*), in particular from the fruit of the blueberry, and a concentrate from raspberry (*Rubus idaeus*), in particular from the fruit of the raspberry, and a concentrate of blackberry (*Rubus* spp.), especially the fruit of the blackberry, and a concentrate of chokeberry (*Aronia*, in particular *Aronia melanocarpa*), especially the fruit of the chokeberry, and a concentrate from spinach (*Spinacia oleracea*), in particular from the leaves of the spinach, and a concentrate from the cherry (*Prunus avium*), in particular from the cherry fruit, and a concentrate from Brussels sprouts (*Brassica oleracea gemmifera*), especially florets of Brussels sprouts.

It cannot be entirely ruled out that concentrates or extracts from other, especially related, plants and other parts of plants may be used in place of individual concentrates or extracts in this list to achieve a similar technical effect.

In certain embodiments, the mixture of fruits, vegetables, and spices contains an extract of green tea (*Camellia sinensis*), in particular of green tea leaves, and/or a concentrate of broccoli (*Brassica oleracea italica*), in particular of seeds, sprouts and/or shoots of broccoli, and/or a concentrate from broccoli (*Brassica oleracea italica*), in particular from florets and/or stems of broccoli, and/or an extract from the onion (*Allium cepa*, in particular *Allium cepa alliaceae*), in particular from the bulb of the onion, and/or an extract from apple (*Malus domestica*), in particular from the apple fruit, in particular from peels of the apple fruit, and/or an extract from acerola (*Malpighia glabra*, in particular *Malpighia glabra linne*), in particular from the fruit of acerola, and/or a concentrate from the tomato (*Lycopersicon esculentum*), in particular from the fruit of the tomato, and/or a concentrate from turmeric (*Curcuma longa*), in particular from the root of turmeric, and/or a concentrate from garlic (*Allium sativum*), in particular from the garlic clove, and/or a concentrate of basil (*Ocimum basilicum*), in particular of basil leaves, and/or a concentrate of oregano (*Origanum vulgare*), in particular of leaves of oregano, and/or a concentrate from the cinnamon tree (*Cinnamomum cassia*), in particular from the bark (without cork) of the cinnamon tree, and/or a concentrate from the carrot (*Dacus carota*, in particular *Dacus carota sativa*), in particular from the root of the carrot, and/or a concentrate from elderberry (*Sambucus nigra*), in particular from the fruit of the elderberry, and/or an extract of the currant (*Ribes*), in particular of the blackcurrant (*Ribes nigrum*), in particular of the fruit of the blackcurrant, and/or a concentrate from the blueberry (*Vaccinium*), in particular from the fruit of the blueberry, and/or a concentrate of raspberry (*Rubus idaeus*), in particular of the fruit of the raspberry, and/or a concentrate from the blackberry (*Rubus* spp.), in particular from the fruit of the blackberry, and/or a concentrate from the chokeberry (*Aronia*, in particular *Aronia melanocarpa*), especially from the fruit of the chokeberry, and/or a concentrate from spinach (*Spinacia oleracea*), in particular from the leaves of the spinach, and/or a concentrate from the cherry (*Prunus avium*), in particular from the cherry fruit, and/or a concentrate from Brussels sprouts (*Brassica oleracea gemmifera*), especially florets of Brussels sprouts.

In preferred embodiments, 100 g of the composition as a dietary supplement for children contains 10 mg to 5000 mg, preferably 50 mg to 4000 mg, of the pepper component, 4 mg to 300 mg, preferably 8 mg to 60 mg, of the curcumin-cyclodextrin mixture, and 50 mg to 1000 mg, preferably 100 mg to 500 mg, of the mixture of fruits, vegetables and spices.

In preferred embodiments, the composition as a dietary supplement for children further comprises one or more components selected from:

Vitamin C, preferably 500 mg to 2000 mg per 100 g;

Niacin, preferably 50 mg to 600 mg per 100 g;

Alpha-tocopheryl acetate, preferably 80 mg to 300 mg per 100 g;

Pantothenic acid, preferably 50 mg to 100 mg per 100 g;

Pyridoxine, preferably 5 mg to 40 mg per 100 g;

Thiamine, preferably 5 mg to 50 mg per 100 g;

Riboflavin, preferably 4 mg to 40 mg per 100 g;

Cyanocobolamine, preferably 10 µg to 50 µg per 100 g;

Folic acid, preferably 0.5 mg to 3 mg per 100 g;

Biotin, preferably 0.2 mg to 1 mg per 100 g;

Beta-carotene, preferably 10 mg to 50 mg per 100 g;

Chromium picolinate and/or chromium trichloride, each preferably 0.5 mg to 5 mg per 100 g;

Selenium-enriched yeast, preferably 50 to 400 mg per 100 g;

Zinc gluconate, preferably 100 mg to 500 mg per 100 g;

Copper(II) gluconate, preferably 20 mg to 80 mg per 100 g;

Cholecalciferol, preferably 50 µg to 250 µg per 100 g;

Trimagnesium citrate, preferably 3 g to 11 g per 100 g;

Calcium hydrogen phosphate, preferably 0.5 g to 3 g per 100 g;

Calcium lactate, preferably 0.2 g to 1.0 g per 100 g;

Milk mineral concentrate, preferably 3 g to 15 g per 100 g;

Inulin, preferably 40 g to 80 g per 100 g.

In preferred embodiments, the composition as a dietary supplement for children further comprises one or more components selected from:

Citric acid, preferably 3 g to 11 g per 100 g;

Steviol glycosides, preferably 0.01 g to 1.0 g per 100 g.

In preferred embodiments, the composition as a dietary supplement for children does not contain an algae component or an extract from ginger.

It is a further object of the disclosure to disclose a method for preparing a composition, a dietary supplement or a composition as a dietary supplement for children. The method comprises:

Providing in a vessel and stirring
- the pepper component,
- the curcumin-cyclodextrin mixture,
- optionally the extract from the ginger (*Zingiber officinale*),
- optionally the algae component and
- the mixture of fruits, vegetables and spices;

The addition of other components and stirring to obtain an intermediate, wherein the addition of at least one component is preferably carried out a) in portions in partial amounts of a total amount of the component and interrupted by stirring or b) continuously with stirring;

Filling of the intermediate product into cans, sachets or capsules.

The providing and adding is preferably carried out in such a way that the pepper component is present in 10 mg to 5000 mg, preferably 50 mg to 4000 mg, per 100 g of intermediate.

The providing and adding is preferably carried out in such a way that the mixture of fruits, vegetables and spices is present in 50 mg to 1000 mg, preferably 100 mg to 500 mg, per 100 g of intermediate.

Optionally, the providing and adding is carried out in such a way that the intermediate contains 1 mg to 1000 mg, preferably 5 mg to 60 mg, of the extract from the ginger (*Zingiber officinale*) per 100 g.

Optionally, the providing and adding is carried out in such a way that the intermediate contains 5 mg to 500 mg, preferably 10 mg to 100 mg, of the algae component per 100 g.

In the preparation of a composition or dietary supplement, the providing and adding is preferably carried out in such a way that the curcumin-cyclodextrin mixture is present in 20 mg to 1000 mg, particularly preferably 80 mg to 400 mg, per 100 g of intermediate. In the preparation of a composition as a dietary supplement for children, the providing and adding is preferably carried out in such a way that the curcumin-cyclodextrin mixture is present in 4 mg to 300 mg, particularly preferably 8 mg to 60 mg, per 100 g of intermediate.

The algae component and the extract from the ginger are preferably optional for the composition. For the composition as a dietary supplement for children, the algae component and the extract from the ginger are not provided.

The addition of at least one component is preferably carried out in portions in partial amounts of a total amount of the component and interrupted by stirring or continuously with stirring. In other words, at least one component is not added all at once, but in such a way that it can gradually mix with the other components. This is particularly relevant for components with a large weight fraction, e.g. fructose or inulin. This can ensure efficient mixing and a homogeneous product.

The disclosure is explained in more detail below with reference to an exemplary embodiment.

In an example of the composition according to the disclosure, 100 g of the composition contains 1000 mg of piperine, 130 mg of curcumin-gamma-cyclodextrin complex, 20 mg of an extract of ginger (*Zingiber officinale*), 33 mg of a powder of brown algae, and 250 mg of a mixture of fruits, vegetables, and spices.

The mixture of fruits, vegetables and spices contains an extract of leaves of green tea (*Camellia sinensis*), a concentrate of broccoli sprouts (*Brassica oleracea italica*), an extract of the bulb of the onion (*Allium cepa*), an extract of peels of apple fruit (*Malus domestica*), an extract from the fruit of acerola (*Malpighia glabra*), a concentrate from the fruit of tomato (*Lycopersicon esculentum*), a concentrate from florets and/or stems of broccoli (*Brassica oleracea italica*), a concentrate from the root of turmeric (*Curcuma longa*), a concentrate from the of garlic clove (*Allium sativum*), a concentrate from basil leaves (*Ocimum basilicum*), a concentrate from oregano leaves (*Origanum vulgare*), a concentrate from the bark (without cork) of the cinnamon tree (*Cinnamonum cassia*), a concentrate from the root of the carrot (*Dacus carota*), a concentrate from fruit of elderberry (*Sambucus nigra*), an extract from fruit of currant (*Ribes*), a concentrate from fruit of blueberry (*Vaccinium*), a concentrate from fruit of raspberry (*Rubus idaeus*), a concentrate from fruit of blackberry (*Rubus* spp.), a concentrate from fruit of chokeberry (*Aronia*), a concentrate from spinach leaves (*Spinacia oleracea*), a concentrate from cherry fruit (*Prunus avium*), an extract from fruit of blueberry (*Vaccinium*) and a concentrate from florets of Brussels sprout (*Brassica oleracea gemmifera*).

To a large extent, the mixture of fruits, vegetables and spices contains an extract from leaves of green tea (about 30% by weight), a concentrate from shoots of broccoli (about 10% by weight), an extract from the bulb of onion (about 9% by weight), an extract from peels of the fruit of the apple (about 9% by weight), an extract from the fruit of the acerola (about 4% by weight), a concentrate from the fruit of the tomato (about 4% by weight), and a concentrate (about 4% by weight) from florets and/or stems of the broccoli. The remaining ingredients are present in 0.1% to 3.5% by weight.

The composition according to the disclosure can also be used to prepare various other compositions and dietary supplements, all of which benefit significantly from the health-promoting and absorption-enhancing properties of the composition according to the disclosure.

Thus, 100 g of the composition of this example further contain:
- Vitamin C, 1000 mg;
- Niacin, 340 mg;
- Caffeine, 200 mg;
- Alpha-tocopheryl acetate, 20 mg;
- Pantothenic acid, 60 mg;
- Pyridoxine, 20 mg;
- Thiamine, 14 mg;
- Riboflavin, 16 mg;
- Cyanocobolamine, preferably 10 μg;
- Folic acid, 2.0 mg;
- Biotin, 1.5 mg;
- Beta-carotene, 13 mg;
- Selenium-enriched yeast, 91 mg;
- Citric acid, 2.6 g;
- Gum arabic, 20 g;
- Vegetable fiber from oats, pea, rice and apple, 17 g;
- Pectin, 1 g;
- Guar gum, 3 g;
- Guarana extract, 3 g;
- Beetroot powder (concentrate of beetroot juice, maltodextrin and citric acid), 0.7 g;
- Lactic acid cultures (*Lactobacillus acidophilus, Lactobacillus reuteri*), 0.3 g;
- Multienzyme complex of amylase, lactase, protease, cellulase, lipase, 0.3 g;
- Inulin, 0.3 g;
- Steviol glycosides, 0.1 g;
- Grape seed extract 6 mg;
- Fructose, ad 100 g.

This example also describes a dietary supplement comprising said composition. In this exemplary embodiment, the composition is present as a dietary supplement in the form of a powder in sachets.

In one example of the composition as a dietary supplement for children according to the disclosure, 100 g of the composition as a dietary supplement for children contains 1000 mg of piperine, 14 mg of curcumin-gamma-cyclodextrin complex, and 270 mg of a mixture of fruits, vegetables, and spices.

The mixture of fruits, vegetables and spices contains an extract of leaves of green tea (*Camellia sinensis*), a concentrate of broccoli sprouts (*Brassica oleracea italica*), an extract of the bulb of the onion (*Allium cepa*), an extract of peels of apple fruit (*Malus domestica*), an extract from the fruit of acerola (*Malpighia glabra*), a concentrate from the fruit of tomato (*Lycopersicon esculentum*), a concentrate from florets and/or stems of broccoli (*Brassica oleracea italica*), a concentrate from the root of turmeric (*Curcuma longa*), a concentrate from the of garlic clove (*Allium sativum*), a concentrate from basil leaves (*Ocimum basilicum*), a concentrate from oregano leaves (*Origanum vulgare*), a concentrate from the bark (without cork) of the cinnamon tree (*Cinnamonum cassia*), a concentrate from the root of the carrot (*Dacus carota*), a concentrate from fruit of elderberry (*Sambucus nigra*), an extract from fruit of currant (*Ribes*), a concentrate from fruit of blueberry (*Vaccinium*), a concentrate from fruit of raspberry (*Rubus idaeus*), a concentrate from fruit of blackberry (*Rubus* spp.), a concentrate from fruit of chokeberry (*Aronia*), a concentrate from spinach leaves (*Spinacia oleracea*), a concentrate from cherry fruit (*Prunus avium*), an extract from fruit of blueberry (*Vaccinium*) and a concentrate from florets of Brussels sprout (*Brassica oleracea gemmifera*).

For the most part, the mixture of fruits, vegetables and spices contains an extract from leaves of green tea (about 30% by weight), a concentrate from shoots of broccoli (about 10% by weight), an extract from the bulb of onion (about 9% by weight), an extract from peels of the fruit of the apple (about 9% by weight), an extract from the fruit of the acerola (about 4% by weight), a concentrate from the fruit of the tomato (about 4% by weight), and a concentrate (about 4% by weight) from florets and/or stems of the broccoli. The remaining ingredients are present in 0.8% by weight to 3.0% by weight. Only a concentrate of florets of Brussels sprouts and an extract of the fruit of blueberry are added to the mixture of fruits, vegetables and spices in smaller amounts (0.1% by weight to 0.3% by weight).

Furthermore, 100 g of this exemplary composition contains as a dietary supplement for children:

Vitamin C, 860 mg;
Niacin, 214 mg;
Alpha-tocopheryl acetate, 143 mg;
Pantothenic acid, 72 mg;
Pyridoxine, 23 mg;
Thiamine, 20 mg;
Riboflavin, 19 mg;
Cyanocobolamine, 29 µg;
Folic acid, 2 mg;
Biotin, 0.4 mg;
Beta-carotene, 29 mg;
Chromium picolinate, 4 mg;
Selenium-enriched yeast, 120 mg;
Zinc gluconate, 265 mg;
Copper(II) gluconate, 46 mg;
Cholecalciferol, 107 µg
Citric acid, 7 g;
Trimagnesium citrate, 7 g;
Calcium hydrogen phosphate, 1.3 g;
Calcium lactate, 0.6 g;
Steviol glycosides, 0.4;
Milk mineral concentrate, 7 g;
Inulin, ad 100 g.

This example describes a composition according to the disclosure as a dietary supplement for children. In this exemplary embodiment, the composition is present as a dietary supplement in the form of a powder in a can.

Lastly, an exemplary method for preparing a composition according to the disclosure will be described. The method comprises:

The provision in a vessel and stirring of
    1000 mg extract from the pepper,
    130 mg of the curcumin-cyclodextrin mixture,
    20 mg of the extract of ginger (*Zingiber officinale*),
    33 mg powder from brown algae and
    250 mg of the mixture of fruits, vegetables and spices;
The addition of 1 g vitamin C and 5 g fructose as further components and stirring. After homogenization by stirring, another 15 g fructose are added and stirring is continued. After further homogenization by stirring, another 15 g fructose is added and stirring is continued. Then the difference ad 100 g in the form of fructose is added and further homogenized by stirring. The obtained powder is filled into sachets.

The method can ensure efficient mixing and a homogeneous product.

The invention claimed is:

1. A composition containing amounts effective for promoting health of:
    a pepper component,
    a curcumin-cyclodextrin mixture, and
    a mixture of fruits, vegetables and spices.

2. The composition according to claim 1, further comprising an algal component.

3. The composition according to claim 1, wherein the composition comprises an extract of ginger (*Zingiber officinale*).

4. The composition according to claim 1, wherein the pepper component is an extract of the pepper (*Piper nigrum*).

5. The composition according to claim 1, wherein the curcumin-cyclodextrin mixture is a curcumin-cyclodextrin complex.

6. The composition according to claim 1, wherein the mixture of fruits, vegetables and spices comprises an extract of green tea (*Camelia sinensis*), a concentrate of broccoli (*Brassica oleracea italica*), an extract from onion (*Allium cepa*), an extract from apple (*Malus domestica*), an extract from acerola (*Malpighia glabra*), a concentrate from tomato (*Lycopersicon* esculentem), a concentrate from turmeric (*Curcuma longa*), a concentrate of garlic (*Allium sativum*), a concentrate of basil (*Ocimum basilicum*), a concentrate of oregano (*Origanum vulgare*), a concentrate of cinnamon (*Cinnamomum cassia*), a concentrate of carrot (*Dacus carota*), a concentrate of elderberry (*Sambucus nigra*), an extract of currant (*Ribes* sp.), a concentrate of blueberry (*Vaccinium* sp.), a concentrate of raspberry (*Rubus idaeus*), a concentrate of blackberry (*Rubus* spp.), a concentrate of chokeberry (*Aronia* sp.), a concentrate of spinach (*Spinacia oleracea*), a concentrate of cherry (*Prunus avium*), an extract of blueberry (*Vaccinium* sp.) and a concentrate of Brussels sprout (*Brassica oleracea gemmifera*).

7. The composition according to claim 1, wherein 100 g of the composition contain
 10 mg to 5000 mg of the pepper component,
 20 mg to 1000 mg of the curcumin-cyclodextrin mixture,
 1 mg to 1000 mg of the extract of ginger (*Zingiber officinale*),
 5 mg to 500 mg of the powder of brown algae, and
 50 mg to 1000 mg of the mixture of fruits, vegetables and spices.

8. The composition according to claim 1, further containing the following components:
 Vitamin C, 500 mg to 2000 mg per 100 g of composition;
 Niacin, 100 mg to 800 mg per 100 g of composition;
 Caffeine, 50 mg to 500 mg per 100 g of composition;
 Alpha-tocopheryl acetate, 20 mg to 300 mg per 100 g of composition;
 Pantothenic acid, 20 mg to 100 mg per 100 g of composition;
 Pyridoxine, 5 mg to 60 mg per 100 g of composition;
 Thiamine, 5 mg to 60 mg per 100 g of composition;
 Riboflavin, 4 mg to 40 mg per 100 g of composition;
 Cyanocobolamine, 4 ug to 20 ug per 100 g of composition;
 Folic acid, 0.5 mg to 5 mg per 100 g of composition;
 Biotin, 0.5 mg to 5 mg per 100 g of composition;
 Beta-carotene, 4 mg to 30 mg per 100 g of composition;
 Selenium-enriched yeast, 10 mg to 500 mg per 100 g of composition;
 Gum arabic, 10 g to 30 g per 100 g of composition;
 Vegetable fiber, from oats, pea, rice and apple, 10 g to 25 g per 100 g of composition;
 Pectin and/or guar gum, totaling 1 to 6 g per 100 g of composition;
 Guarana extract, 1 g to 3 g per 100 g of composition;
 Lactic acid bacterial cultures (*Lactobacillus acidophilus* and *Lactobacillus reuteri*), 0.1 g to 1 g per 100 g of composition;
 Inulin, 0.1 g to 1 g per 100 g of composition; and
 Grape seed extract, 1 mg to 20 mg per 100 g of composition.

9. The composition according to claim 1, further containing the following components:
 Citric acid, 1 g to 5 g per 100 g of composition;
 Fructose, 20 g to 70 g per 100 g of composition;
 Beetroot powder (concentrate of beetroot juice, maltodextrin and citric acid), 0.1 g to 2 g per 100 g of composition;
 Multienzyme complex of amylase, lactase, protease, cellulase, lipase, 0.1 g to 1 g per 100 g of composition; and
 Steviol glycosides, 0.01 g to 0.5 g per 100 g of composition.

10. A dietary supplement, containing the composition according to claim 1.

11. A composition that is a dietary supplement for children, containing amounts effective for promoting health of:
 a pepper component,
 a curcumin-cyclodextrin mixture, and
 a mixture of fruits, vegetables and spices.

12. The composition according to claim 11, wherein 100 g contain
 10 mg to 5000 mg of the pepper component,
 20 mg to 1000 mg of the curcumin-cyclodextrin mixture, and
 50 mg to 1000 mg of the mixture of fruits, vegetables and spices.

13. The composition according to claim 11, further containing one or more components selected from the group consisting of:
 Vitamin C, preferably 500 mg to 2000 mg per 100 g;
 Niacin, preferably 50 mg to 600 mg per 100 g;
 Alpha-tocopheryl acetate, 80 mg to 300 mg per 100 g;
 Pantothenic acid, 50 mg to 100 mg per 100 g;
 Pyridoxine, 5 mg to 40 mg per 100 g;
 Thiamine, 5 mg to 50 mg per 100 g;
 Riboflavin, 4 mg to 40 mg per 100 g;
 Cyanocobolamine, 10 ug to 50 ug per 100 g; and
 Folic acid, 0.5 mg to 3 mg per 100 g;
 Biotin, 0.2 mg to 1 mg per 100 g;
 Beta-carotene, 10 mg to 50 mg per 100 g;
 Chromium picolinate and/or chromium trichloride, each 0.5 mg to 5 mg per 100 g;
 Selenium-enriched yeast, 50 to 400 mg per 100 g;
 Zinc gluconate, 100 mg to 500 mg per 100 g;
 Copper (II) gluconate, 20 mg to 80 mg per 100 g;
 Cholecalciferol, 50 ug to 250 ug per 100 g;
 Trimagnesium citrate, 3 to 11 g per 100 g;
 Calcium hydrogen phosphate, 0.5 to 3 g per 100 g;
 Calcium lactate, 0.2 g to 1.0 g per 100 g;
 Milk mineral concentrate, 3 g to 15 g per 100 g; and
 Inulin, 40 g to 80 g per 100 g.

14. The composition according to claim 11, further containing one or more components selected from the group consisting of:
 Citric acid, 3 to 11 g per 100 g; and
 Steviol glycosides, 0.01 g to 1.0 g per 100 g.

15. A method for preparing the composition according to claim 1, comprising:
 providing in a vessel and stirring
 the pepper component,
 the curcumin-cyclodextrin mixture, and
 the mixture of fruits, vegetables and spices; wherein the stirring is intermittent or continuous, and
 filling the stirred mixture into cans, sachets or capsules.

* * * * *